US007150995B2

(12) United States Patent
Xie et al.

(10) Patent No.: US 7,150,995 B2
(45) Date of Patent: Dec. 19, 2006

(54) METHODS AND SYSTEMS FOR POINT OF CARE BODILY FLUID ANALYSIS

(75) Inventors: Zongcen Charles Xie, Sunnyvale, CA (US); Jeffrey A. Pierce, Redwood City, CA (US); Carole R. Stivers, Palo Alto, CA (US)

(73) Assignee: Metrika, Inc., Sunnyvale, CA (US)

( * ) Notice: Subject to any disclaimer, the term of this patent is extended or adjusted under 35 U.S.C. 154(b) by 38 days.

(21) Appl. No.: 10/759,547

(22) Filed: Jan. 16, 2004

(65) Prior Publication Data

US 2005/0158866 A1 Jul. 21, 2005

(51) Int. Cl.
*G01N 33/72* (2006.01)
(52) U.S. Cl. ........................................ 436/67
(58) Field of Classification Search ................ 422/61; 436/518, 67
See application file for complete search history.

(56) References Cited

U.S. PATENT DOCUMENTS

| | | | |
|---|---|---|---|
| 2,387,244 A | 10/1945 | Compton | |
| 3,419,000 A | 12/1968 | Phillips | |
| 3,536,927 A | 10/1970 | Mink | |
| 3,552,928 A | 1/1971 | Fetter | |
| 3,620,676 A | 11/1971 | Ward | |
| 3,663,374 A | 5/1972 | Moyer et al. | |
| 3,770,382 A | 11/1973 | Carter et al. | |
| 3,993,451 A | 11/1976 | Verbeck | |
| 4,038,485 A | 7/1977 | Johnston et al. | |
| 4,039,652 A | 8/1977 | Adams et al. | |
| 4,046,514 A | 9/1977 | Johnston et al. | |
| 4,053,281 A | 10/1977 | Carter | |
| 4,094,647 A | 6/1978 | Deutsch et al. | |
| 4,096,138 A | 6/1978 | Scherr | |
| 4,100,268 A | 7/1978 | Scherr | |
| 4,129,417 A | 12/1978 | White | |
| 4,133,639 A | 1/1979 | Harte | |
| 4,160,008 A | 7/1979 | Fenocketti et al. | |
| 4,168,146 A | 9/1979 | Grubb et al. | |
| 4,169,138 A | 9/1979 | Jonsson | |
| 4,181,636 A | 1/1980 | Fisher | |
| 4,210,723 A | 7/1980 | Dorman et al. | |

(Continued)

FOREIGN PATENT DOCUMENTS

CA 2019865 A1 1/1991

(Continued)

OTHER PUBLICATIONS

Surfynol® 400 Series, Liquid, Nonionic Surface-Active Agents Surfynol® 440, 465, 485, Air Products and Chemicals, Inc. Performance Chemicals (Product Brochure).

(Continued)

*Primary Examiner*—Jill Warden
*Assistant Examiner*—Natalia Levkovich
(74) *Attorney, Agent, or Firm*—Gordon & Rees LLP

(57) ABSTRACT

The invention provides a system for quantitative measurement of percent glycated hemoglobin as hemoglobin A1c in whole blood having extended shelf life at room temperature. The system comprising a blood dilution solution and a device adapted for receiving at least a portion of diluted blood solution, for contacting the blood solution with a dry reagent system, for detecting a change in the reagent system and for providing an indication of the analytical result to the user, and the extended shelf life and the elimination of a requirement for refrigeration for storage is achieved by having the blood dilution solution which comprises a first surfactant for hemolysis and a second surfactant for stability. The system of this invention is useful in other analysis kits and systems as well.

12 Claims, 4 Drawing Sheets

U.S. PATENT DOCUMENTS

| | | |
|---|---|---|
| 4,219,529 A | 8/1980 | Tersteeg et al. |
| 4,224,032 A | 9/1980 | Glover et al. |
| 4,233,402 A | 11/1980 | Maggio et al. |
| 4,235,601 A | 11/1980 | Deutsch et al. |
| 4,248,829 A | 2/1981 | Kitajima et al. |
| 4,275,149 A | 6/1981 | Litman et al. |
| 4,281,061 A | 7/1981 | Zuk et al. |
| 4,288,228 A | 9/1981 | Oberhardt |
| 4,288,541 A | 9/1981 | Magers et al. |
| 4,301,412 A | 11/1981 | Hill et al. |
| 4,302,536 A | 11/1981 | Longnecker |
| 4,313,734 A | 2/1982 | Leuvering |
| 4,315,890 A | 2/1982 | Tamers |
| 4,361,537 A | 11/1982 | Deutsch et al. |
| 4,366,241 A | 12/1982 | Tom et al. |
| 4,373,932 A | 2/1983 | Gribnau et al. |
| 4,376,110 A | 3/1983 | David et al. |
| 4,419,453 A | 12/1983 | Dorman et al. |
| 4,425,438 A | 1/1984 | Bauman et al. |
| 4,435,504 A | 3/1984 | Zuk et al. |
| 4,446,232 A | 5/1984 | Liotta |
| 4,477,575 A | 10/1984 | Vogel et al. |
| 4,517,288 A | 5/1985 | Giegel et al. |
| 4,518,259 A | 5/1985 | Ward |
| 4,547,460 A | 10/1985 | Eikenberry |
| 4,549,655 A | 10/1985 | Korsythe et al. |
| 4,552,458 A | 11/1985 | Lowne |
| 4,552,839 A | 11/1985 | Gould et al. |
| 4,575,621 A | 3/1986 | Dreifus |
| 4,594,327 A | 6/1986 | Zuk |
| 4,595,439 A | 6/1986 | Boger et al. |
| 4,608,246 A | 8/1986 | Bayer et al. |
| 4,615,340 A | 10/1986 | Cronenberg et al. |
| 4,627,445 A | 12/1986 | Garcia et al. |
| 4,636,479 A | 1/1987 | Martin et al. |
| 4,637,403 A | 1/1987 | Garcia et al. |
| 4,637,978 A | 1/1987 | Dappen |
| 4,652,517 A * | 3/1987 | Scholl et al. .................. 435/5 |
| 4,654,310 A | 3/1987 | Ly |
| 4,673,657 A | 6/1987 | Christian |
| 4,703,017 A | 10/1987 | Campbell et al. |
| 4,713,165 A | 12/1987 | Conover et al. |
| 4,719,338 A | 1/1988 | Avery et al. |
| 4,731,726 A | 3/1988 | Allen et al. |
| 4,734,360 A | 3/1988 | Phillips |
| 4,740,468 A | 4/1988 | Weng et al. |
| 4,744,760 A | 5/1988 | Molday |
| 4,753,776 A | 6/1988 | Hillman et al. |
| 4,756,828 A | 7/1988 | Litman et al. |
| 4,756,884 A | 7/1988 | Hillman et al. |
| 4,757,004 A | 7/1988 | Houts et al. |
| 4,761,381 A | 8/1988 | Blatt et al. |
| 4,774,192 A | 9/1988 | Terminiello |
| 4,787,398 A | 11/1988 | Garcia et al. |
| 4,790,979 A | 12/1988 | Terminiello et al. |
| 4,791,461 A | 12/1988 | Kishimoto et al. |
| 4,806,312 A | 2/1989 | Greenquist |
| 4,816,224 A | 3/1989 | Vogel et al. |
| 4,843,020 A | 6/1989 | Woodford |
| 4,853,335 A | 8/1989 | Olsen et al. |
| 4,855,240 A | 8/1989 | Rosenstein et al. |
| 4,857,453 A | 8/1989 | Ullman et al. |
| 4,861,711 A | 8/1989 | Friesen et al. |
| 4,868,108 A | 9/1989 | Bahar |
| 4,883,688 A | 11/1989 | Houts et al. |
| 4,883,764 A | 11/1989 | Kloepfer |
| 4,913,881 A | 4/1990 | Evers |
| 4,923,800 A | 5/1990 | Ly |
| 4,927,769 A | 5/1990 | Chang et al. |
| 4,935,147 A | 6/1990 | Ullman et al. |
| 4,935,339 A | 6/1990 | Zahradnik |
| 4,935,346 A | 6/1990 | Phillips et al. |
| 4,943,522 A | 7/1990 | Eisinger et al. |
| 4,943,525 A | 7/1990 | Dawson |
| 4,945,205 A | 7/1990 | Litman et al. |
| 4,956,302 A | 9/1990 | Gordon et al. |
| 4,959,307 A | 9/1990 | Olson |
| 4,959,324 A | 9/1990 | Ramel et al. |
| 4,960,691 A | 10/1990 | Gordon et al. |
| 4,973,549 A | 11/1990 | Khanna et al. |
| 4,981,786 A | 1/1991 | Dafforn et al. |
| 4,987,085 A | 1/1991 | Allen et al. |
| 4,995,402 A | 2/1991 | Smith et al. |
| 4,999,285 A | 3/1991 | Stiso |
| 4,999,287 A | 3/1991 | Allen et al. |
| 5,004,582 A | 4/1991 | Miyata et al. |
| 5,004,583 A | 4/1991 | Guruswamy et al. |
| 5,006,474 A | 4/1991 | Horstman et al. |
| 5,029,583 A | 7/1991 | Meserol et al. |
| 5,030,558 A | 7/1991 | Litman et al. |
| 5,035,704 A | 7/1991 | Lambert et al. |
| 5,036,000 A | 7/1991 | Palmer et al. |
| 5,037,614 A | 8/1991 | Makita et al. |
| 5,037,645 A | 8/1991 | Strahilevitz |
| 5,039,607 A | 8/1991 | Skold et al. |
| 5,049,487 A | 9/1991 | Phillips et al. |
| 5,059,394 A | 10/1991 | Phillips et al. |
| 5,064,541 A | 11/1991 | Jeng et al. |
| 5,064,618 A | 11/1991 | Baker et al. |
| 5,073,344 A | 12/1991 | Smith et al. |
| 5,073,484 A | 12/1991 | Swanson et al. |
| 5,075,078 A | 12/1991 | Osikowiez et al. |
| 5,077,017 A | 12/1991 | Gorin et al. ................ 422/100 |
| 5,079,174 A | 1/1992 | Buck et al. |
| 5,087,556 A | 2/1992 | Ertinghausen |
| 5,089,053 A * | 2/1992 | Chou et al. .................... 134/7 |
| 5,089,391 A | 2/1992 | Buechler et al. |
| 5,091,153 A | 2/1992 | Bachand |
| 5,096,669 A | 3/1992 | Lauks et al. |
| 5,096,837 A | 3/1992 | Fan et al. |
| 5,104,619 A | 4/1992 | de Castro et al. |
| 5,110,724 A | 5/1992 | Hewett |
| 5,114,350 A | 5/1992 | Hewett |
| 5,114,859 A | 5/1992 | Kagenow |
| 5,120,643 A | 6/1992 | Ching et al. |
| 5,126,247 A | 6/1992 | Palmer et al. |
| 5,126,276 A | 6/1992 | Fish et al. |
| 5,132,086 A | 7/1992 | Allen et al. |
| 5,135,716 A | 8/1992 | Thakore |
| 5,135,719 A | 8/1992 | Hillman et al. |
| 5,139,685 A | 8/1992 | de Castro et al. |
| 5,141,850 A | 8/1992 | Cole et al. |
| 5,141,875 A | 8/1992 | Kelton et al. |
| 5,145,645 A | 9/1992 | Zakin et al. |
| 5,149,622 A | 9/1992 | Brown |
| 5,155,025 A | 10/1992 | Allen et al. |
| 5,164,294 A | 11/1992 | Skold et al. |
| 5,168,042 A | 12/1992 | Ly |
| 5,171,688 A | 12/1992 | Hewett et al. |
| 5,173,433 A | 12/1992 | Bachand |
| 5,174,963 A | 12/1992 | Fuller et al. |
| 5,177,789 A | 1/1993 | Covert |
| 5,179,005 A | 1/1993 | Phillips et al. |
| 5,192,947 A | 3/1993 | Neustein |
| 5,200,317 A | 4/1993 | Georgevich |
| 5,200,321 A | 4/1993 | Kidwell |
| 5,202,268 A | 4/1993 | Kuhn et al. |
| 5,204,063 A | 4/1993 | Allen |
| 5,208,147 A | 5/1993 | Kagemow et al. |
| 5,212,060 A | 5/1993 | Maddox |
| 5,213,965 A | 5/1993 | Jones |
| 5,215,886 A | 6/1993 | Patel et al. |
| 5,218,312 A | 6/1993 | Moro |
| 5,223,219 A | 6/1993 | Subramanian et al. |

| | | |
|---|---|---|
| 5,223,220 A | 6/1993 | Fan et al. |
| 5,231,035 A | 7/1993 | Akers, Jr. |
| 5,232,668 A | 8/1993 | Grant et al. |
| 5,234,593 A | 8/1993 | Kuroki et al. |
| 5,234,813 A | 8/1993 | McGeehan et al. |
| 5,248,619 A | 9/1993 | Skold et al. |
| 5,248,772 A | 9/1993 | Siiman et al. |
| 5,250,439 A | 10/1993 | Musho et al. |
| 5,262,067 A | 11/1993 | Wilk et al. |
| 5,264,180 A | 11/1993 | Allen et al. |
| 5,308,581 A | 5/1994 | Lippitsch et al. |
| 5,310,469 A | 5/1994 | Cunningham et al. |
| 5,334,513 A | 8/1994 | Skold et al. |
| 5,340,539 A | 8/1994 | Allen et al. |
| 5,354,692 A | 10/1994 | Yang et al. |
| 5,401,466 A | 3/1995 | Foltz et al. |
| 5,401,636 A | 3/1995 | Craig |
| 5,409,664 A | 4/1995 | Allen |
| 5,415,994 A | 5/1995 | Imrich |
| 5,416,000 A | 5/1995 | Allen et al. |
| 5,423,989 A | 6/1995 | Allen et al. |
| 5,424,035 A | 6/1995 | Hones et al. |
| 5,426,030 A | 6/1995 | Rittersdorf et al. |
| 5,427,915 A | 6/1995 | Ribi et al. |
| 5,439,647 A | 8/1995 | Saini |
| 5,445,967 A | 8/1995 | Deuter |
| 5,451,504 A | 9/1995 | Fitzpatrick |
| 5,451,507 A | 9/1995 | Skold et al. |
| 5,458,852 A | 10/1995 | Buechler |
| 5,459,080 A | 10/1995 | Adamezyk et al. |
| 5,464,587 A | 11/1995 | Lippitsch et al. |
| 5,468,606 A | 11/1995 | Bogart et al. |
| 5,468,647 A | 11/1995 | Skold et al. |
| 5,501,949 A | 3/1996 | Marshall |
| 5,512,492 A | 4/1996 | Herron et al. |
| 5,527,712 A | 6/1996 | Sheehy |
| 5,541,069 A | 7/1996 | Mortensen et al. |
| 5,541,117 A | 7/1996 | Karl et al. ............... 436/518 |
| 5,552,064 A | 9/1996 | Chachowski et al. |
| 5,563,042 A | 10/1996 | Phillips et al. |
| 5,569,608 A | 10/1996 | Sommer |
| 5,571,725 A | 11/1996 | Pohl et al. |
| 5,580,794 A | 12/1996 | Allen ...................... 436/169 |
| 5,582,907 A | 12/1996 | Pall |
| 5,605,662 A | 2/1997 | Heller et al. |
| 5,607,863 A | 3/1997 | Chandler |
| 5,637,469 A | 6/1997 | Wilding et al. |
| 5,643,721 A * | 7/1997 | Spring et al. ................ 435/6 |
| 5,753,519 A | 5/1998 | Durst et al. |
| 5,837,546 A | 11/1998 | Allen et al. ............... 436/169 |
| 5,882,935 A * | 3/1999 | Hirai et al. ............... 436/67 |
| 5,932,480 A | 8/1999 | Maruo et al. ............... 436/66 |
| 5,945,345 A | 8/1999 | Blatt et al. ............... 436/518 |
| 5,968,839 A | 10/1999 | Blatt et al. ............... 436/518 |
| 5,981,294 A | 11/1999 | Blatt et al. ............... 436/178 |
| 6,043,043 A | 3/2000 | Yip .......................... 435/7.2 |
| 6,050,956 A | 4/2000 | Ikegami et al. ............ 600/573 |
| 6,066,620 A * | 5/2000 | McGregor et al. ........... 514/12 |
| 6,162,645 A | 12/2000 | Lee et al. .................. 436/67 |
| 6,174,734 B1 | 1/2001 | Ito et al. ................. 436/518 |
| 6,235,239 B1* | 5/2001 | Sharma ..................... 422/28 |
| 6,258,045 B1 | 7/2001 | Ray et al. |
| 6,316,265 B1 | 11/2001 | Lee et al. ................. 436/67 |
| 2002/0142017 A1* | 10/2002 | Simonnet .................. 424/401 |

FOREIGN PATENT DOCUMENTS

| | | |
|---|---|---|
| CA | 2020029 A1 | 1/1991 |
| CA | 2028968 A1 | 5/1991 |
| EP | 0125118 A2 | 11/1984 |
| EP | 0182647 A2 | 5/1986 |
| EP | 0217403 A2 | 4/1987 |
| EP | 0257400 A2 | 3/1988 |
| EP | 0284232 A1 | 9/1988 |
| EP | 0317070 A2 | 5/1989 |
| EP | 0323605 A2 | 7/1989 |
| EP | 0330517 A2 | 8/1989 |
| EP | 0342913 A2 | 11/1989 |
| EP | 0357400 A2 | 3/1990 |
| EP | 0421294 A2 | 4/1991 |
| EP | 0430395 A1 | 6/1991 |
| GB | 2090659 A | 7/1982 |
| WO | WO 8001515 A1 | 7/1980 |
| WO | WO 8300931 A1 | 3/1983 |
| WO | WO 8501354 A1 | 3/1985 |
| WO | WO 8808534 A1 | 11/1988 |
| WO | WO 9010869 A1 | 9/1990 |
| WO | WO 9114942 A1 | 10/1991 |
| WO | WO 9201226 A1 | 1/1992 |
| WO | WO 9201498 A2 | 2/1992 |
| WO | WO 9303175 A1 | 2/1993 |
| WO | WO 9427137 A1 | 11/1994 |
| WO | WO 9506240 A1 | 3/1995 |
| WO | WO 9746868 A1 | 12/1997 |

OTHER PUBLICATIONS

Pluronic & Tetronic Surfactants, BASF Corporation Specialty Products (Product Brochure).

ABSTRACT: Application of the Boehringer Mannheim Hemoglobin A1c Assay on the Olympus AU800™, J. Murakami et al.

*A1c Now*, Metrika Inc., (Professional-Use Product Insert).

Hawkes, et al., "A Dot-Immunobinding Assay for Monoclonal and Other Antibodies," Analytical Biochemistry, Jan. 1, 1982, vol. 119, No. 1, pp. 142-147.

Sharon, et al., "Detection of Specific Hybridoma Clones by Replica Immunoadsorption of Their Secreted Antibodies," Proc. Natl. Acad. Sci. USA, Mar. 1979, vol. 76, No. 3, pp. 1420-1424.

"Home Cholesterol Testing", Lancet, Dec. 5, 1992, vol. 340, No. 8832, p. 1386.

Daviaud, et al., "Reliability and Feasibility of Pregnancy Home-Use Tests: Laboratory Validation and Diagnostic Evaluation by 638 Volunteers," Clin. Chem. 1993, vol. 39, No. 1, pp. 53-59.

Van Oudheusden, et al., "A Multilayaer membrane System for Blood Plasma Isolation for Use in Primary Health care", Ann Clin Biochem., 1991, vol. 28, pp. 55-59.

Allen, et al., "Instrument-Free Quantitative Test Systems", Applications of Diagnostics, 1990, pp. 147-176.

Pradella et al., "Three-Minute Whole-Blood Cholesterol Screening Test Evaluated" Clin. Chem., 1990, vol. 36, No. 11, pp. 1994-1995.

Zuk, et al., "Enzyme Immunochromatography-A Quantitative Imminoassay Requiring No Instrumentation," 1985, Clin. Chem. vol. 31, No. 7, pp. 1144-1150.

Allen et al., "A Noninstrumentated Quantitative Test System and Its Application for Determining Cholesterol Concentration in Whole Blood," Clin. Chem. 1990, vol. 36, No. 9, pp. 1591-1597.

Free et al., "Dry Chemistry Reagent Systems," Lab. Med., Sep. 1984, vol. 15, No. 9, pp. 595-601.

Free et al., "Simple Specific Test for Urine Glucose," Clin. Chem. 1957, vol. 3, No. 3, pp. 163-168.

Comer, "Semiquantitative Specific Test Paper for Glucose in Urine," Anal. Chem. Nov. 1956, vol. 28, No. 11, pp. 1748-1750.

Free et al., "A Simple Test For Urine Bilrubin," Gastroenterology, Jul. 1953, vol. 24, No. 3, pp. 414-421.

Free et al., "Self Testing, An Emerging Component of Clinical Chemistry," Clin. Chem. 1984, vol. 30, No. 6, pp. 829-838.

Balazs, et al., "Use of Test Strips with Colour Meter to Measure Blood-Glucose," Lancet, Jun. 6, 1970, vol. 1, No. 7658, p. 1232.

Free, "Instrumentation for Bedside Information—Progress and Challenges," Pure Appl. Chem., 1982, vol. 54, No. 11, pp. 2063-2073.

Levomson, et al., "Salt Effects on Antigen-Antibody Kinetics," Biochemistry, 1/201970, vol. 9, No. 2, pp. 322-331.

Prefilled Poly-Prep Columns for Ion Exchange Chromatography Instruction Manual, 7 pages, Bio-Rad Laboratories, Hercules, CA.

Millitrap, pp. 8-10, Waters Technical Service, Mitford, MA.

Nova-Clean IC, Bulletin #264, 7 pages, Alltech Associates, Deerfield, IL.

"Installation Instructions and Troubleshooting Guide for OnGuard Cartridges", Feb. 17, 1995, pp. 1-16, Dionex, Sunnvale, CA.

"Varian Sample Preparation Catalog, Bond Elut and Mega Bond Elut", Jun. 11, 1997, pp. 1-29, Varian Associates, Palo Alto, CA.

Joyce, et al., "Trace Level Determination of Bromate in Ozonated Drinking Water Using Ion Chromatography," J. Chromatogr. A, Jun. 10, 1994, vol. 671, No. 1-2, pp. 165-171.

Kunz, "Miniature integrated Optical modules for chemical and biochemical sensing", Sensors and Actuators B, Jan. 1997, vol. 38-39, No. 1-3, pp. 13-28.

Muller et al., "Antigen controlled Immuno Diagnosis-'Acid Test'," J. Immun. Methods, Oct. 16, 1980, vol. 37, No. 2, pp. 185-190.

* cited by examiner

METHODS AND SYSTEMS FOR POINT OF CARE BODILY FLUID ANALYSIS

RELATED APPLICATIONS

The subject matter of this application is related to diagnostic devices, systems and chemistry, and in particular is related to the disposable single-use digital electronic instruments that are entirely self-contained, including all chemistry reagents, as disclosed in U.S. application Ser. No. 08/455,236 entitled "Novel Disposable Electronic Assay Device" filed May 31, 1995 by Michael P. Allen and now U.S. Pat. No. 5,580,794; U.S. application Ser. No. 08/657,894 entitled "Electronic Assay Device and Method" filed Jun. 7, 1996 by Michael P. Allen, Joel M. Blatt, and Joseph T. Widunas and now U.S. Pat. No. 5,837,546; U.S. application Ser. No. 08/564,441 entitled "Device For Blood Separation in a Diagnostic Device" filed Nov. 29, 1995 by Joel M. Blatt, Wilma M. Mangan, Paul J. Patel and Michael P. Allen and now U.S. Pat. No. 5,981,294; U.S. application Ser. No. 08/645,453 entitled "Method and Device Producing a Predetermined Distribution of Detectable Change in Assays" filed May 13, 1996 by Joel M. Blatt, Michael P. Allen and Paul J. Patel, now U.S. Pat. No. 5,968,839 and U.S. application Ser. No. 08/703,479 filed Aug. 27, 1996 by Joel M. Blatt, Wilma M. Mangan, Paul J. Patel and Victor A. Manneh, now U.S. Pat. No. 5,945,345. The above patents have the same assignee as the present invention and this application, and are incorporated herein by reference in their entirety.

FIELD OF THE INVENTION

This invention relates to diagnostic devices and systems used for qualitative and quantitative determination of analytes in bodily fluids, such as blood and urine.

BACKGROUND OF THE INVENTION

There has been a proliferation of analytical and diagnostic devices known as "point of care" devices. These devices are used professionally in clinics, doctors' offices, and hospitals, and are used by individual consumers for glucose, glycated hemoglobin, pregnancy and other tests. These devices are well known in the art and typically include a reagent pad in the form of a strip or built into a device for receiving a bodily fluid sample, and a meter or indicator device for giving the user a readout of the analysis results, such as glucose level, or a color indication of a condition present or not present, such as, pregnancy. In some cases the device is part of a test kit or system, which also includes a sample preparation portion, such as a sample dilution vial and solution.

Some of the point of care devices and kits have limited shelf life, including some devices and kits that are best kept under refrigeration, e.g., below about 10° C., in order to provide useful shelf life, particularly in the consumer or individual use market. For example, the METRIKA® A1c test kit (available from Metrika, Inc., Sunnyvale, Calif.) for glycated hemoglobin testing is recommended for storage under refrigeration in order to provide a one year shelf life. Without refrigeration, the Metrika A1c test kit is recommended for use within one month.

Thus, there is a need for improvement in point of care diagnostic devices and test kits to provide extended shelf life and in particular for extended shelf life without refrigeration.

SUMMARY OF THE INVENTION

This invention provides a system for quantitative measurement of percent glycated hemoglobin as hemoglobin A1c in whole blood comprising a blood dilution solution and a device adapted for receiving at least a portion of diluted blood solution, for contacting the blood solution with a dry reagent system, for detecting a change in the reagent system and for providing an indication of the analytical result to the user, wherein the blood dilution solution comprises a first surfactant for hemolysis and a second surfactant for stability. In a particular aspect this invention provides said system wherein the first surfactant is a zwitterionic surfactant and the second surfactant is a nonionic surfactant.

In another aspect, this invention provides a composition for dilution of a bodily fluid for analysis comprising a first surfactant for modification of an analyte in the fluid and a second surfactant for stability. The composition further comprises a bodily fluid in mixture with a first surfactant for modification of an analyte in the fluid and a second surfactant for stability, and in particular wherein the first surfactant is a zwitterionic surfactant and the second surfactant is a nonionic surfactant.

In another aspect, this invention provides a method of preparing a whole blood sample for analysis comprising diluting the blood sample with a solution comprising a first surfactant for hemolysis and a second surfactant for stability. The diluted blood sample is contacted with a dry immunoassay reagent system. In a particular aspect this invention provides said method wherein first surfactant is a zwitterionic surfactant and the second surfactant is a nonionic surfactant.

In another aspect, this invention provides a system for detection of an analyte in a liquid sample comprising a sample dilution solution and a device adapted for receiving at least a portion of diluted sample solution, for contacting the sample solution with a dry reagent system, for detecting a change in the reagent system and for providing an indication of the analytical result to the user, and wherein the sample dilution solution comprises a first surfactant for modification of the analyte and a second surfactant for stability. In a particular aspect, this invention provides said system wherein first surfactant is a zwitterionic surfactant and the second surfactant is a nonionic or an ionic surfactant. In another particular aspect, this invention provides said system wherein the first surfactant is a nonionic surfactant and the second surfactant is a zwitterionic surfactant or an ionic surfactant. In another particular aspect, this invention provides said system wherein the first surfactant is an ionic surfactant and the second surfactant is a zwitterionic surfactant or a nonionic surfactant.

DESCRIPTION OF THE INVENTION

Figure 1:
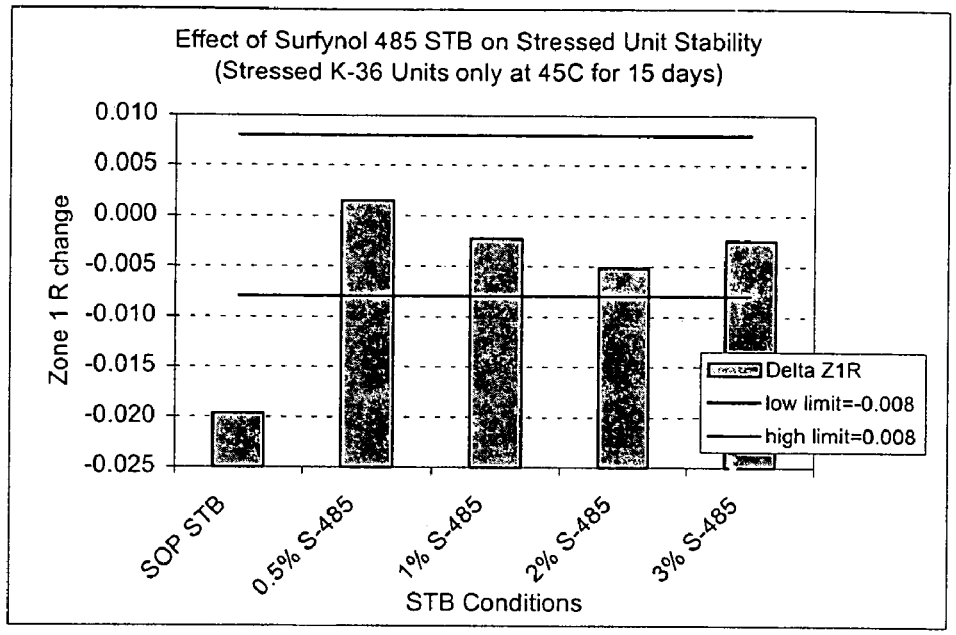
FIGS. 1 and 2 show the effect of a nonionic surfactant on stability of a test unit.

This invention provides an improvement in stability and shelf life for a variety of diagnostic devices, systems and kits. It is particularly useful in those devices and systems that employ a dry reagent test site and is preferred for use in such devices and systems employ a dry reagent system, particularly immunoassay reagent systems, which are commonly used in such devices and systems. This invention is implemented by providing a novel dilution solution for sample preparation prior to analysis. Conventional dilution solutions for sample preparation for dry reagent systems contain a single surfactant or a single type of surfactant for modification or preparation of the analyte in the sample fluid to provide compatibility and/or reactivity with the reagent system in the test device or test strip. It has now been found that when, in addition to the surfactant for modification or preparation of the analyte, a second surfactant is included, the dilution solution provides for increased stability and increased shelf life of the system as a whole. Thus, this invention includes modification of the sample dilution solution, which in turn provides increased stability and extended shelf life of the whole system comprising the dry immunoassay reagent system. As a result, the entire kit comprising the dilution solution, the dry reagent system and the reading device can exhibit extended shelf life at room temperature, without the need for low temperature storage to obtain the extended shelf life.

Disclosure and description of the invention will be in the context of blood analysis, particularly glycated hemoglobin (% HbA1c) testing systems known in the art. However, it will be apparent to one skilled in the art that this invention can be adapted to other systems to increase system stability and shelf life, particularly those systems that employ dry latex particle type reagent systems. The problem solved by the improvement of this invention is that over time, certain diagnostic and test systems degrade in accuracy to the point where they are unreliable and unusable. Different diagnostic systems have different stability and shelf life characteristics. It has been found that in a hemoglobin A1c test system, incorporating a nonionic surfactant as stabilizer with the conventional zwitterionic surfactant as a hemolysis agent, provides a system that substantially improves shelf life at room temperature. This invention is expected to enable reasonable shelf life with the elimination of the refrigeration requirement for such test systems.

The dry reagent systems for which this invention is useful in extending shelf life and stability of the analysis system or kit are those which comprise a binding pair assay in the form of particulate labels. Preferred systems are non-enzymatic binding assays, that typically include antigen-antibody pair systems, and which preferably provide chromatographic indications. The typical rapid chromatographic tests utilize either a "sandwich" assay or a "competition" assay to detect the presence of a desired analyte. In the sandwich assay, an analyte is bound, or "sandwiched," between an unlabeled first binding partner and a labeled second binding partner. For example, an analyte, such as a protein hormone, can be captured by a first binding partner, in this case, a first antibody immobilized on a membrane. The analyte-first antibody complex can then be detected by a second binding partner having a label, such as a second antibody tagged with a colored particle. In contrast, during the competition assay, the analyte in the sample competes with a labeled analyte, or labeled analogue to the analyte, for a binding partner immobilized on a solid support. A greater concentration of analyte in the sample results in a lower signal in the assay, as the labeled analytes are competed away from the binding partner on the solid support (i.e., the signal produced during a competition assay decreases as the concentration of analyte in the sample increases). Thus, the sandwich assay can provide a qualitative or quantitative assessment with great sensitivity, while the competition assay provides a quantitative measure of analyte concentration over a broad range with less sensitivity. In these dry reagent systems a preferred form is microparticulate labels, and in particular latex particle systems.

The present invention is useful in assays which use specific binding members. A specific binding partner or member, as used herein, is a member of a specific binding pair—that is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies, and antibody fragments, both monoclonal and polyclonal, and complexes thereof, including those formed by recombinant DNA molecules. The term hapten, as used herein, refers to a partial antigen or non-protein binding member which is capable of binding to an antibody, but which is not capable of eliciting antibody formation unless coupled to a carrier protein.

Analyte, as used herein, is the substance to be detected which may be present in the test sample. The analyte can be any substance for which there exists a naturally occurring specific binding member (such as, an antibody), or for which a specific binding member can be prepared. Thus an analyte is a substance that can bind to one or more specific binding members in an assay. Analyte also includes any antigenic substances, haptens, antibodies, macromolecules, and combinations thereof. As a member of a specific binding pair, the analyte can be detected by means of naturally occurring specific binding partners (pairs) such as the use of intrinsic factor protein as a member of a specific binding pair for the determination of Vitamin B12, or the use of lectin as a member of a specific binding pair for the determination of a carbohydrate. The analyte can include a protein, a peptide, an amino acid, a hormone, a steroid, a vitamin, a drug including those administered for the therapeutic purposes as well as those administered for illicit purposes, a bacterium, a virus, and metabolites of or antibodies to any of the above substances. In particular, such analytes include, but are not intended to be limited to, ferritin; creatinine kinase MIB (CK-MB); digoxin; phenytoin; phenobarbital; carbamazepine; vancomycin; gentamicin; theophylline; valproic acid; quinidine; luteinizing hormone (LH); follicole stimulating hormone (FSH); estradiol, progesterone; IgE antibodies; vitamin B2 microglobulin; glycated hemoglobin (Gly. Hb); cortisol; digitoxin; N-acetylprocainamide (NAPA); procainamide; antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis Be antigen (HbeAg); antibodies to hepatitis Be antigen (Anti-Hbe); thyroid stimulating hormone (TSH); throxine (T4); total triiodothyronine (Total T3); free triiodothyronine (Free T3); carcinoembryoic antigen (CEA); and alpha fetal protein (AFP). Drugs of abuse and referenced substances include, but are not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methaqualone; opiates such as heroin, morphine, codeine, hydromorphone, hydrocodone, methadone, oxycodone, oxymorphone, and opium; phenylcyclidine; and propoxyphene. The details for the preparation of such antibodies and the suitability for use as specific binding members are well known to those skilled in the art.

The analyte-analog can be any substance which cross-reacts with the analyte-specific binding member, although it may do so to a greater or lesser extent than does the analyte itself. The analyte-analog can include a modified analyte as well as a fragmented or synthetic portion of the analyte molecule, so long as the analyte-analog has at least one epitope site in common with the analyte of interest. An example of an analyte-analog is a synthetic peptide sequence which duplicates at least one epitope of the whole-molecule analyte so that the analyte-analog can bind to an analyte-specific binding member.

The test sample can be derived from any biological source, such as a physiological fluid, including whole blood or whole blood components including red blood cells, white blood cells, platelets, serum and plasma; ascites; urine; sweat; milk; synovial fluid; mucous; peritoneal fluid; amniotic fluid; pericerebrospinal fluid; and other constituents of the body which may contain the analyte of interest. The test sample can be pretreated prior to use, such as preparing plasma from blood, diluting viscous fluids, or the like; methods of treatment can involve filtration, distillation, concentration, inactivation of interfering compounds, and the addition of reagents. Besides physiological fluids, other liquid samples can be used such as water, food products and the like for performance of environmental or food production assays.

This invention is described in the context of the tests discussed below and illustrated in FIGS. 1–8. For example, in the A1c test kits used, the sample dilution or sample preparation solution contains ferricyanide in a buffered solution containing a zwitterionic surfactant. The purpose of the dilution buffer solution is to dilute the whole blood sample and to lyse the red blood cells. The zwitterionic surfactant is the hemolytic agent that lyses the red blood cells. It has been found that adding a nonionic surfactant, forming a dilution solution composition containing two different surfactants, results in improved stability of the test kit and improved shelf life of the test kit. The amount of nonionic surfactant useful in this particular application of the invention can be from at least about 0.01% w/v (weight of surfactant per volume of initial solution) up to an amount that may interfere with the function of the hemolytic agent or the specific binding assay. In general, the amount of nonionic surfactant that will provide desired stability and shelf life improvement can be from about 0.01% to about 10% w/v, preferably from about 0.1% to about 7% w/v, more preferably from about 0.2% to about 5% w/v and most preferably from about 0.3% to about 4% w/v. As seen from the Test Examples below, in this particular test kit, levels of 0.5% and 1.0% w/v provide excellent stability and shelf life improvement.

In general application of this invention, one skilled in the art can determine what type of surfactant is used or is useful in the sample preparation solution, i.e., the surfactant that reacts with or converts the analyte to a form needed for the assay to be performed. Once the type of surfactant is determined, the selection of a different type surfactant to provide stability and shelf life enhancement will be apparent to one skilled in the art. As disclosed above, if the analyte modifying surfactant is a zwitterionic surfactant, then the second surfactant can be a nonionic and/or ionic surfactant, whichever provides the desired improved stability of the system. If the analyte modifying surfactant is a nonionic surfactant, then the second surfactant can be a zwitterionic and/or ionic surfactant, whichever provides the desired improved stability of the system. If the analyte modifying surfactant is an ionic surfactant, then the second surfactant can be a nonionic and/or zwitterionic surfactant, whichever provides the desired improved stability of the system. The amount of the first analyte modifying surfactant in a particular system will be determined by the analyte content in the sample to be tested. The amount of the second stabilizing surfactant will range from about 0.001% to about 15% w/v, about 0.01% to about 10% w/v, about 0.05% to about 8% w/v or about 0.1% to about 5% w/v. Formulations for a particular test kit and application can be devised following the disclosure herein and by straightforward testing, as illustrated in the following Test Examples.

The selection of surfactants according to this invention will likewise be within the skill or the art following the disclosure herein. For example, in the test examples below, the stabilizing surfactant can be a compatible nonionic surfactant, such as the SURFYNOL® liquid nonionic surfactants (available from Air Products and Chemicals, Inc., Allentown, Pa.), particularly the 400 Series, such as the 440, 465 and 485 products, which are ethoxylated acetylenic glycols. The chemical nomenclature for SURFYNOL® surfactant is ethoxylated-2,4,7,9-tetramethyl-5-decyne-4,7-diol. The SURFYNOL® surfactants have variable ethylene oxide contents. For the 400 Series, the ethylene oxide content is varied from 40 to 85% by weight. The 440, 465 and 485 surfactants have ethylene oxide contents of 40, 65 and 85%, respectively. Other surfactants can be selected from the PLURONIC® and TETRONIC® lines of surfactants (available from BASF Performance Chemicals, Parsippany, N.J.), particularly the "L Series" EO-PO-EO type or the "R Series" PO-EG-PO type. PLURONIC® and TETRONIC® surfactants are block copolymers of ethylene oxide and propylene oxide. The "L Series" EO-PO-EO surfactants are polyethylene oxide-polypropylene oxide-polyethylene oxide triblock copolymers. The "R Series" PO-EO-PO surfactants are polypropylene oxide-polyethylene oxide-polypropylene oxide triblock copolymers. Other commercially available surfactants for formulation according to this invention will be known to one skilled in the art.

TEST EXAMPLES

This invention was tested using standard METRIKA A1c test kits available from Metrika, Inc., Sunnyvale, Calif. The test kits, as supplied, include the Sample Dilution Buffer, which contains a hemolytic zwitterionic surfactant, which is ZWITTERGENT® 3-14 available from Roche Applied Science, Roche Diagnostics Corporation, Indianapolis, Ind. The chemical nomenclature for ZWITTERGENT® 3-14 is N-hexadecyl-N,N-dimethyl-3-amino-1-propanesulfonate. Some of the test kits were used as supplied for comparison, and some of the test kits were modified by adding a nonionic surfactant to the Sample Dilution Buffer solution in the amount shown in the following test results. The surfactant selected for the tests was SURFYNOL® 485 nonionic surfactant available from Air Products and Chemicals, Inc., Allentown, Pa.

Figure 2:
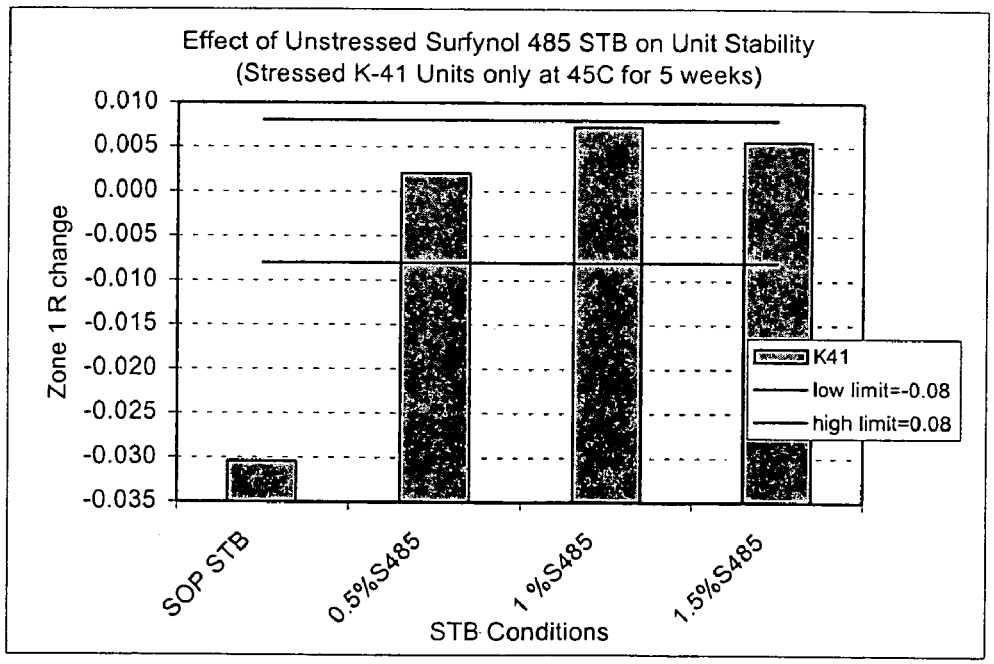

The experimental results are shown in the FIGS. 1–8. The y-axis for FIGS. 1 and 2 is "Zone 1 R change" which is the difference between reflectance values for Zone 1 (the HbA1c immunoassay zone) obtained from units stressed at 45° C. versus 2–8° C. In these experiments, A1c units were stressed at 45° C. and 2–8° C. for 15 days. Stressing at 45° C. is commonly used as an accelerated means of assessing product stability. The projected shelf life at room temperature is typically a multiple of the shelf life at 45° C. The "units" referred to herein are the METRIKA® A1c monitor that provides a port for receiving the diluted blood sample, the reagent test zones built into the unit, and an LED readout for providing the user the results of the test. "STB" is the Sample Treatment Buffer, also referred to above as the Sample Dilution Buffer. "SOP STB" is the standard Sample Dilution Buffer as conventionally used in the A1c kits, without addition of the nonionic surfactant. The STB, itself, was not stressed for the tests shown in FIGS. 1 and 2. As can be seen for both lots K-36 (Lot Number 0307213), FIG. 1, and K-41 (Lot Number A3-06-010), FIG. 2, addition of SURFYNOL® 485 to the STB restored unit performance to its original level prior to stress—when tested with a fresh whole blood sample and assuming no change in performance for the 2–8° C. condition. This was true for a range of SURFYNOL® 485 concentration from 0.5% to 3.0% w/v (weight of SURFYNOL® 485 per volume of SOP STB).

Figure 3:
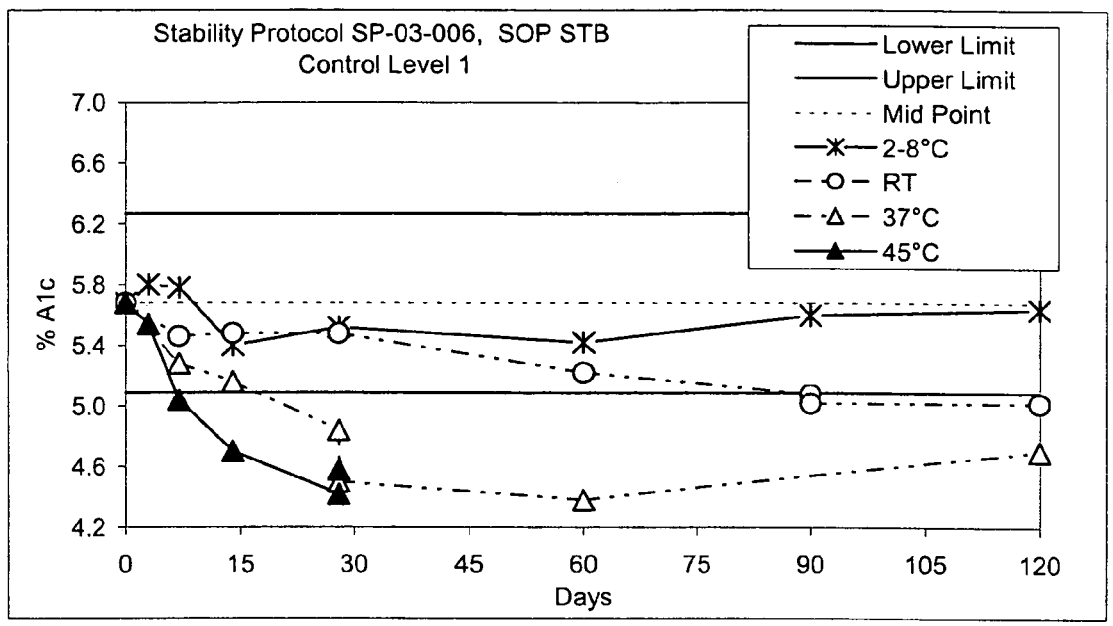
FIGS. 3 and 4 show the stability of the test kit using the sample treatment buffer without the nonionic surfactant added.
Figure 4:
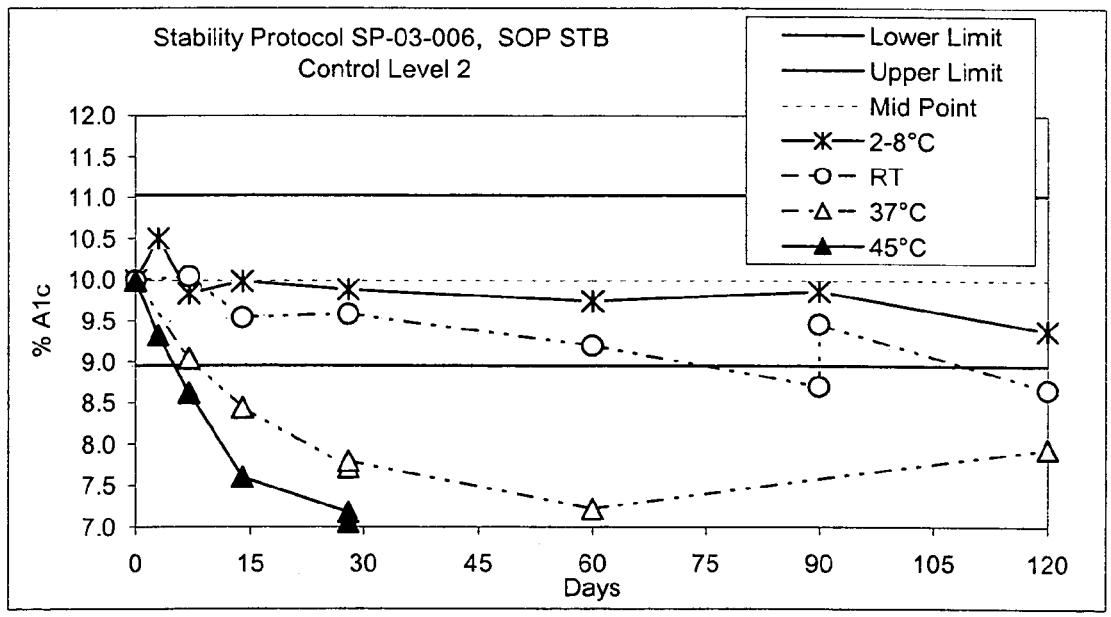
Figure 5:
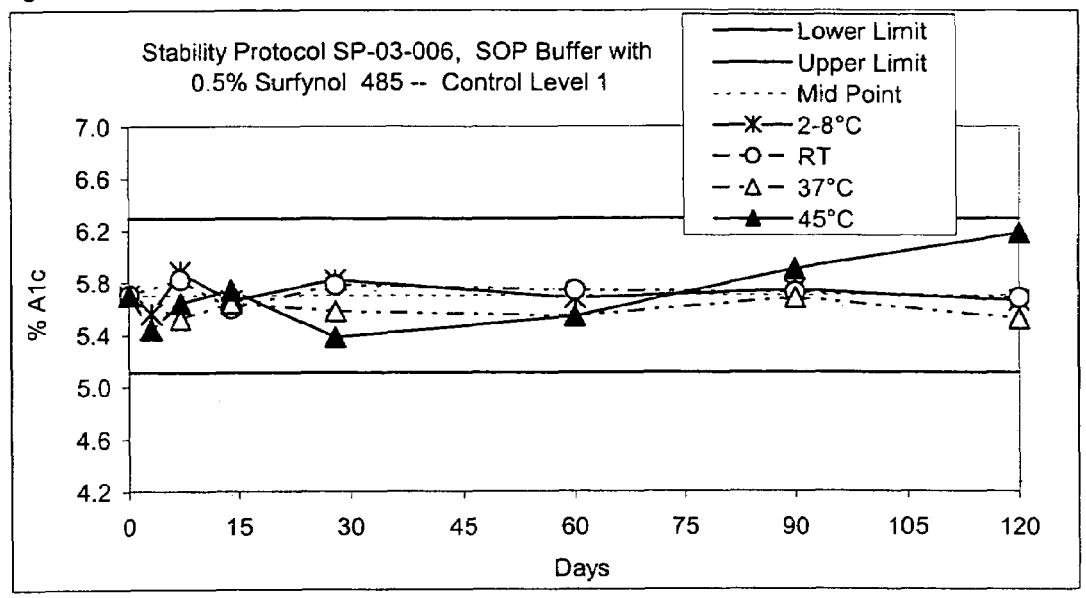
FIGS. 5–8 show the stability of the test kit using the sample treatment buffer with the nonionic surfactant present in different amounts.
Figure 6:
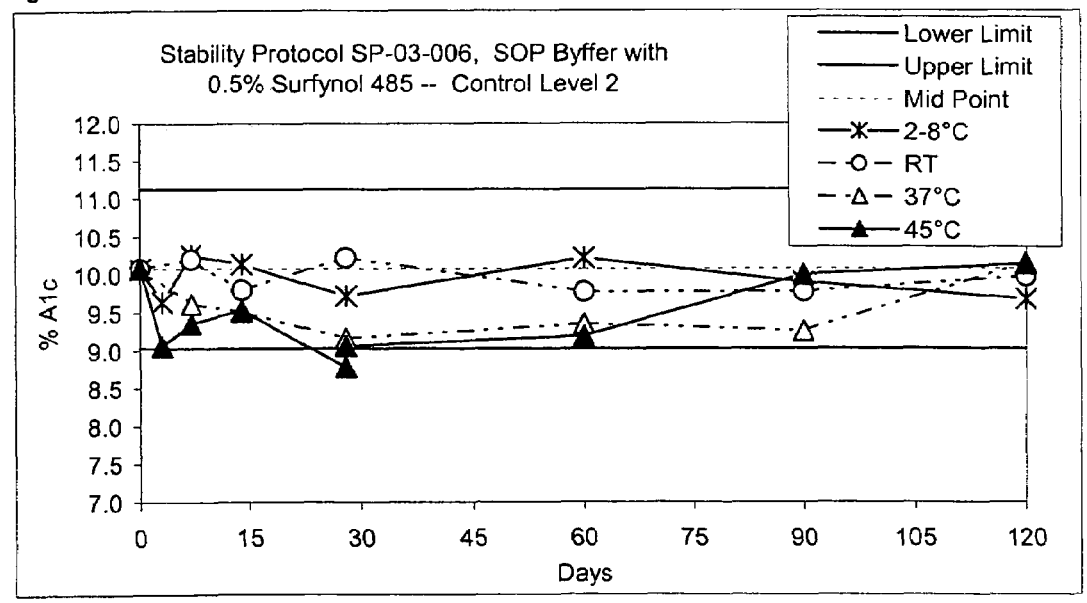
Figure 7:
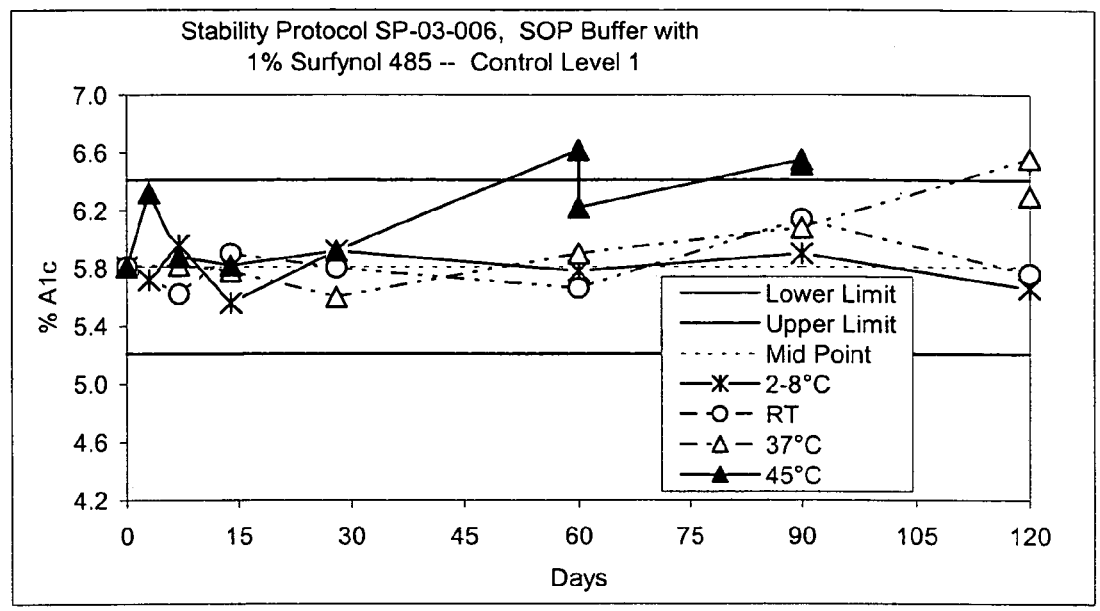
Figure 8:
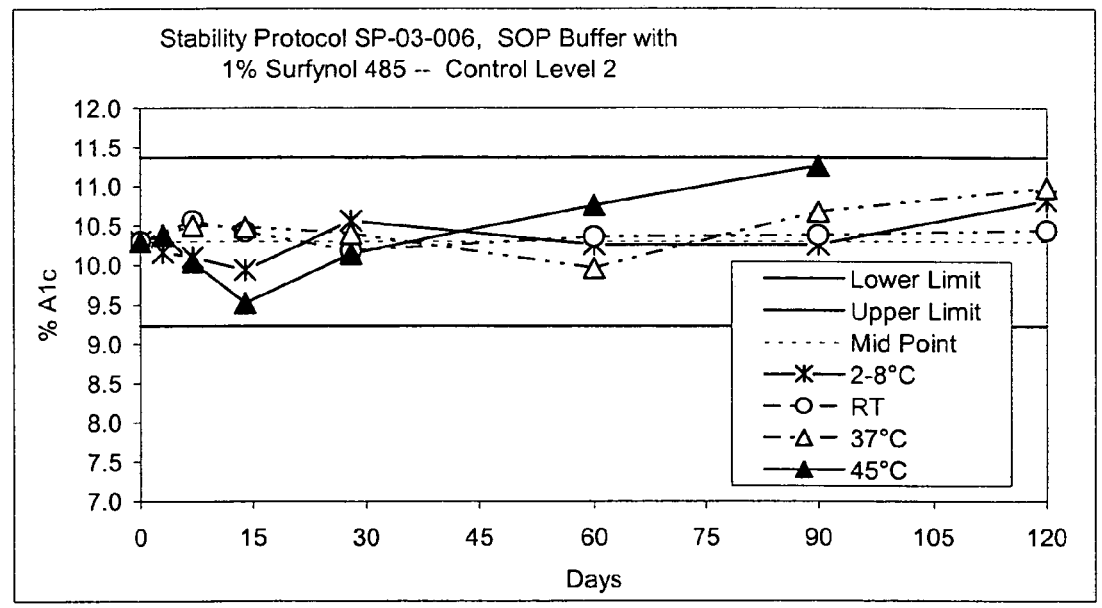

A more extensive and detailed study, Stability Protocol SP-03-006, was performed next (with K-50, Lot Number 0316004) to establish the impact of the two lowest Surfynol® 485 concentrations from the previous experiment on stability for up to four months. Lyphocheck A1c Controls from Bio-Rad Laboratories, Inc., Hercules, Calif., Levels 1 and 2, were used for testing at each time point to detect any potential change in accuracy for different regions of the assay's dynamic range. These results are shown in FIGS. 3–8. The y-axis for these figures is "% A1c" which is the ratio of HbA1c concentration to total hemoglobin concentration, expressed as a percentage. The SOP buffer (STB without added surfactant) failed after 3 to 7 days at 45° C.—as has been commonly observed in the past, with room temperature stability being compromised at about 3 months (FIGS. 3 and 4). In contrast, 45° C. stability was improved to 3–4 months when 0.5%–1.0% was SURFYNOL® 485 was added to the STB (FIGS. 5–8). Room temperature stability exceeded 4 months and, as a result of the approximately tenfold enhanced 45° C. stability, is expected to remain stable for several-fold longer. Unlike the earlier study, in these tests both the units and the STB samples were stressed under the same conditions.

Other details of selection of surfactant combinations for use in this invention will be apparent to one skilled in the art following the disclosure herein. The scope of this invention is defined by the following claims.

We claim:

1. A system for quantitative measurement of percent glycated hemoglobin in whole blood, comprising:
   a blood dilution solution;
   a dry immunoassay reagent system; and
   a device adapted for:
      receiving at least a portion of diluted blood solution;
      contacting the blood solution with the dry immunoassay reagent system for detecting a change in the reagent system; and
      providing an indication of the analytical result to the user;
   wherein the blood dilution solution comprises N-tetradecyl-N,N-dimetyl-3-ammonio-1-propanesulfonate, and a nonionic surfactant selected from the group consisting of an ethoxylated acetylenic glycol polymer, and a block copolymer of ethylene oxide and propylene oxide;
   wherein the blood dilution solution is not in contact with the dry immunoassay reagent system during storage.

2. A system according to claim 1, wherein the dry immunoassay reagent system comprises microparticulate labels.

3. A system according to claim 2, wherein the microparticulates are latex particles.

4. A system for detection of an analyte in a liquid sample comprising:
   a sample dilution solution;
   a dry non-enzymatic binding assay reagent system; and
   a device adapted for:
      receiving at least a portion of diluted sample solution;
      contacting the sample solution with the dry non-enzymatic binding assay reagent system adapted for indicating a change in the reagent system; and
      providing an indication of the analytical result to the user;
   wherein the blood dilution solution comprises N-hexadecyl-N, N-dimethyl-3-amino-1-propanesulfonate, and a nonionic surfactant selected from the group consisting of an ethoxylated acetylenic glycol polymer, and a block copolymer of ethylene oxide and propylene oxide;
   wherein the sample dilution solution is not in contact with the dry non-enzymatic binding assay reagent system during storage.

5. A system according to claim 4, wherein the dry non-enzymatic binding assay reagent system comprises microparticulate labels.

6. A system according to claim 5, wherein the microparticulates are latex particles.

7. The system according to claim 1, wherein the ethoxylated acetylenic glycol polymer is ethoxylated-2,4,7,9-tetramethyl-5-decyne-4,7-diol.

8. The system according to claim 7, wherein the ethoxylated-2,4,7,9-tetramethyl-5-decyne-4,7-diol has an ethylene oxide content of from about 40 to about 85% by weight.

9. The system according to claim 1, wherein the block copolymer of ethylene oxide and propylene oxide is a polyethylene oxide-polypropylene oxide-polyethylene oxide triblock copolymer or a polypropylene oxide-polyethylene oxide-polypropylene oxide triblock copolymer.

10. The system according to claim 4, wherein the ethoxylated acetylenic glycol polymer is ethoxylated-2,4,7,9-tetramethyl-5-decyne-4,7-diol.

11. The system according to claim 10, wherein the ethoxylated-2,4,7,9-tetramethyl-5-decyne-4,7-diol has an ethylene oxide content of from about 40 to about 85% by weight.

12. The system according to claim 4, wherein the block copolymer of ethylene oxide and propylene oxide is a polyethylene oxide-polypropylene oxide-polyethylene oxide triblock copolymer or a polypropylene oxide-polyethylene oxide-polypropylene oxide triblock copolymer.

* * * * *